United States Patent
Arai et al.

(10) Patent No.: US 7,570,734 B2
(45) Date of Patent: Aug. 4, 2009

(54) METHOD AND APPARATUS FOR X-RAY IMAGE CORRECTION

(75) Inventors: Yoshinori Arai, Kyoto (JP); Masakazu Suzuki, Kyoto (JP)

(73) Assignees: J. Morita Manufacturing Corporation, Kyoto (JP); Nihon University, Tokyo (JP)

( * ) Notice: Subject to any disclaimer, the term of this patent is extended or adjusted under 35 U.S.C. 154(b) by 205 days.

(21) Appl. No.: 10/894,218

(22) Filed: Jul. 19, 2004

(65) Prior Publication Data
US 2005/0047552 A1 Mar. 3, 2005

(30) Foreign Application Priority Data
Jul. 25, 2003 (JP) ............................ P2003-280055

(51) Int. Cl.
A61B 6/03 (2006.01)
(52) U.S. Cl. .................... 378/18; 378/205; 378/207
(58) Field of Classification Search ............... 378/205, 378/210, 18, 207
See application file for complete search history.

(56) References Cited

U.S. PATENT DOCUMENTS 6,466,638 B1 * 10/2002 Silver et al. .................. 378/4
6,529,575 B1 * 3/2003 Hsieh ........................... 378/4

FOREIGN PATENT DOCUMENTS

| JP | 2001-224586 | 8/2001 |
| JP | 2002-291726 | 10/2002 |
| JP | 2002-336237 | 11/2002 |

OTHER PUBLICATIONS

Silver et al., Determination and Correction of the Wobble of a C-arm gantry, Proc. SPIE vol. 3979, p. 1459-1468, Medical Imaging 2000; Kenneth M. Hanson, Ed., Jun. 2000.*

Sen et al., Automated detection of small spherical pellets with gradient filtering on digitized XRII images, Proc. SPIE vol. 3979, p. 1452-1458, Medical Imaging 2000; Kenneth M. Hanson, Ed., Jun. 2000.*

Hein et al., Distortion Correction Table for Volume X-ray CT Applications, Proc. SPIE vol. 3977, p. 620-631, Medical Imaging 2000; James T. Dobbins III, John M. Boone, Ed., Apr. 2000.*

(Continued)

*Primary Examiner*—Edward J Glick
*Assistant Examiner*—John M Corbett
(74) *Attorney, Agent, or Firm*—William L. Androlia; H. Henry Koda

(57) ABSTRACT

In an X-ray computerized tomography scanner, a correction phantom embedding an X-ray absorbing object is put on or around a non-vertical rotary axis between an X-ray source and a two-dimensional X-ray detector, and two dimensional imaging data of the phantom is acquired. Then a locus of the X-ray absorbing material is determined in the two-dimensional imaging data, and based on the locus an ideal locus is obtained in the direction of the rotary axis. Next, a difference between the calculated position of the ideal locus and a measured position is determined in the direction of the rotary axis. The difference is used to correct deviation in the direction of the rotary axis.

8 Claims, 6 Drawing Sheets

OTHER PUBLICATIONS

Song et al., Development and evaluation of a MicroCT system for small animal imaging, Nov. 2001, IEEE 2001 Nuclear Science Conference Record, vol. 3, pp. 1600-1604.*

Noo et al., Analytic Method based on identification of ellipse parameters for scanner calibration in cone-beam tomography, 2000, Phys. Med. Biol., vol. 45, pp. 3489-3508.*

Karolczak et al., Implementation of a cone-beam reconstruction algorithm for the single-circle source orbit with embedded misalignment correction using homogeneous coordinates, 2001, Medical Physics, vol. 28, No. 10, pp. 2050-2069.*

Koppe et al., 3D Vessel Reconstruction Based on Rotational Angiography, CARS 95 Proceedings, pp. 101-107.*

* cited by examiner

METHOD AND APPARATUS FOR X-RAY IMAGE CORRECTION

FIELD OF THE INVENTION

The invention relates to X-ray computerized tomography scanner and in particular to correction of an X-ray CT image.

RELATED ART

A typical X-ray computerized tomography (CT) scanner has a gantry having an X-ray source and an X-ray detector both mounted to a rotary component thereof so as to oppose each other. A person to be examined lying on a bed movable vertically and horizontally is positioned between the X-ray source and the X-ray detector. While the gantry is rotated around the person on the bed, a cone beam of X-rays is generated by the X-ray source moving along a circular orbit to irradiate the person, and X-rays transmitting the person are received by the X-ray detector. In the case of a helical CT scanner, X-ray imaging is continued while the person on the bed is kept moving. The detection data are calculated to reconstruct an X-ray tomography image of the person, and the reconstructed image is displayed on a display device.

A gantry of an X-ray CT scanner may have a C arm holding an X-ray source and an X-ray detector (for example, Japanese Patent laid open Publication 2001-224586). The X-ray source and the X-ray detector are mounted at an end and at the other end of the C arm, respectively, while a person to be examined is positioned on a bed between the X-ray source and the X-ray detector. Then the C arm is rotated around the person to move the X-ray source and the X-ray detector along a circular orbit, and X-rays transmitting the person are detected. This type of CT scanner has an advantage that medical staffs can access the person from various directions.

An X-ray CT scanner for dentistry irradiates a person to be examined locally to provide an X-ray tomography image of a local portion or a part of the person (for example Japanese Patent laid open Publication 2002-336237). In such a CT scanner, a gate-like frame made of a very high rigidity is fixed on a base. It supports a rotary arm which is a C arm rotating around a vertical axis. The rotary arm holds an X-ray source and an X-ray detector opposing to each other and interposing the person. The X-ray source and the X-ray detector are moved in a horizontal plane when the rotary arm is rotated. A person to be examined sitting on a chair can be moved in three axes of up-to-down, left-to-right and front-to-back directions, so that a center of a local portion inside the person matches with the rotary center of the rotary arm. In this state, the X-ray source generates an X-ray cone beam irradiating only the local portion in the person. When the arm is rotated, the X-ray source and the X-ray detector are rotated around the person in an angle range according to the imaging condition. An X-ray tomography image of the person is reconstructed based on the detection data, and it is displayed on a display device.

In the above-mentioned X-ray CT scanners, the gantry and the bed (or the chair) are fixed to the base. Though such large-scale X-ray CT scanners fixed to the base are used generally, a portable CT scanner is needed for medical uses and the like. A portable CT scanner is expected to be used easier and in various ways. A CT scanner for imaging a local portion has a possibility that it is made compact and portable. A portable CT scanner may be realized, for example, by using a C arm gantry having a horizontal rotary axis. However, there are many problems to be solved in order to use a portable CT scanner actually. One of the problems is correction of a tomography image due to position shifts of the X-ray source and the X-ray detector. An image has to be reconstructed by correcting the image data for the position shifts.

Various correction techniques on the position shift have been proposed for X-ray CT scanners. For example, a CT scanner disclosed in Japanese Patent laid open Publication 2002-291726 uses a circular gantry. It corrects deviations due to shifts of a two-dimensional X-ray detector, an angle of a detector plane, rotation of the detector plane and so on. A position sensor and an angular velocity sensor are used to detect a change in the detection plane of the two-dimensional X-ray detector, and the position of the X-ray detector is determined based on the change. This correction can also be applied to a C-arm CT scanner.

A CT scanner disclosed in Japanese Patent laid open Publication 2001-224586 uses a C arm gantry having a horizontal rotary axis. It corrects fluctuations of the C arm gantry during rotation caused by irregularities such as vibrations due to rotation, distortion due to gravitation and mechanical vibrations. A correction phantom having many beads arranged helically is used for correcting data. Based on the image of the correction phantom, the positions of the beads are determined. The correction values can be derived by solving equations on conical projection. When data is acquired, an image is corrected with the correction values.

A CT scanner disclosed in Japanese Patent laid open Publication 2002-236237 uses a C arm gantry having a vertical rotary axis. A correction phantom embedding two balls is put in the rotation center and is imaged. The loci of the balls are detected to correct distortion.

SUMMARY OF THE INVENTION

An object of the invention is to acquire X-ray image data correctly in an X-ray CT scanner using a rotary arm which holds an X-ray source and an X-ray detector and is rotated around a non-vertical axis.

In a method according to the invention an X-ray image obtained by the X-ray computerized tomography scanner is corrected. A correction phantom made of an X-ray transmitting material and embedding an X-ray absorbing object (preferably a spherical object) therein is put around the non-vertical (for example, horizontal) rotary axis between a X-ray source and a two-dimensional X-ray detector, and two dimensional imaging data of the correction phantom is acquired by the CT scanner. The imaging data extends in a direction of the rotary axis of the rotary arm and in another direction perpendicular to the rotary axis. Then a locus of the X-ray absorbing material is determined in the two-dimensional imaging data, and an ideal locus of the X-ray absorbing material is obtained in the direction of the rotary axis based on the locus in the two-dimensional imaging data. Next, a difference is determined between the calculated position of the ideal locus and a measured position of the X-ray absorbing material in the direction of the rotary axis. The difference is used to correct deviation in the direction of the rotary axis.

Preferably, when the ideal locus is determined, a width r of deviation is determined in a direction perpendicularly to the rotary axis in the locus, an average $z_B$ of deviation of the locus of the X-ray absorbing material is determined in the direction of the rotary axis, and a rotation angle θ of the rotary arm is determined based on the locus. Then, a position $z_p$ of the locus is calculated in the direction of the rotary axis according to a following relationship:

$$Z_P = \frac{\overline{FS} * Z_B}{\overline{OF} + r \cdot \sin\theta},$$

wherein FS is distance from focal point F of the X-ray source to the imaging plane, OF is distance from the rotary axis to the focal point, and θ is rotation angle of the rotary arm.

An advantage of the invention is that an X-ray image can be acquired correctly in an X-ray CT scanner having a rotary arm rotated around a non-vertical axis.

Another advantage of the invention is that image data can be calculated simply and fast.

BRIEF EXPLANATION OF THE DRAWINGS

These and other objects and features of the present invention will become clear from the following description taken in conjunction with the preferred embodiments thereof with reference to the accompanying drawings, and in which.

PREFERRED EMBODIMENTS OF THE INVENTION

Figure 1:
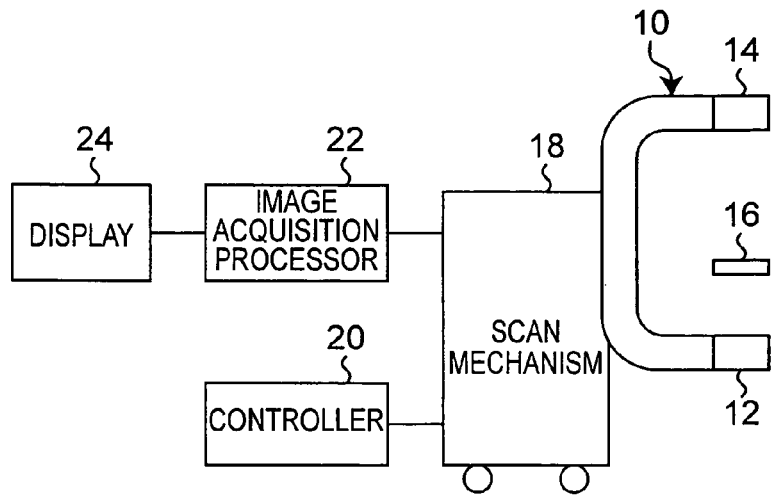
FIG. 1 is a block diagram of a portable X-ray CT scanner.

Referring now to the drawings, wherein like reference characters designate like or corresponding parts throughout the several views, FIG. 1 shows a portable X-ray CT scanner using a rotary arm 10 having a horizontal rotary axis. The rotary arm 10 has a shape similar to transversely tilted character U including two right-angle portions. In such a scanner, an X-ray source 12 is mounted at an end of the rotary arm 10, and a two-dimensional X-ray detector 14 is mounted at the other end of the rotary arm 10. The X-ray source 12 generates a cone beam of X-rays. The two-dimensional X-ray detector 14 is for example an X-ray photomultiplier. It receives incident X-rays to generate visible light which is imaged with a charge-coupled device (CCD) camera and outputs electric signals. A head rest 16 to support a person's head to be examined is positioned around a rotation center between the X-ray source 12 and the X-ray detector 14. This CT scanner is used for dentistry, and the person's head fixed on the head rest 16 is irradiated locally with X-rays. While the cone beam X-rays generated by the X-ray source 12 exposes the person, the X-rays transmitting the head are detected by the two-dimensional X-ray detector 14. The rotary arm 10 is supported at the center thereof by a scan mechanism 18, which rotates it around the rotation axis. In this example, the rotation axis is non-vertical, in concrete horizontal. The scan mechanism 18 on wheels can be moved, and it is fixed for imaging in accordance to the head rest 16. A controller 20 controls the scan mechanism 18 to rotate the rotary arm 10 within a predetermined imaging range. A motor (not shown) in the scan mechanism 18, an axis thereof being connected directly to the rotation center of the rotary arm 10, rotates the rotary arm at a constant speed or at a variable speed. The rotation position can be determined along time axis.

An X-ray image is obtained by irradiating only a local region to be imaged, or a part of the person to be examined, with the cone beam X-rays generated by the X-ray source 12, while the rotary arm 10 having the X-ray source 12 and the X-ray detector 14 opposing to each other is rotated around the person. The rotation control of the rotary arm 10 is similar to a prior art scanner, and it is not explained in detail here. The detection signals of the two-dimensional X-ray detector 14 are sent through the scan mechanism 18 to an image acquisition processor 22 and are stored there in a storage device. An X-ray image is calculated based on the acquired data, and three-dimensional X-ray absorption coefficients in the local region are calculated to reconstruct an image. The reconstructed image is shown in the display apparatus 24. In the example shown in FIG. 1, the rotary arm 10 has the form of transversely tilted character U including two right-angle portions. However, it may have a form of character C or the like.

Figure 2:
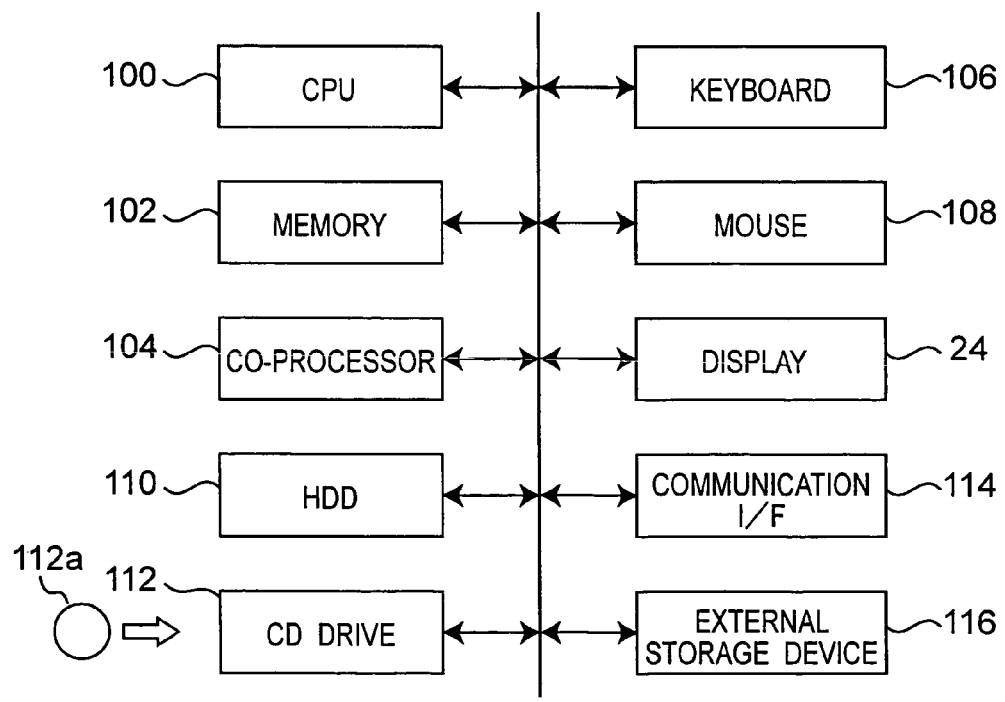
FIG. 2 is a block diagram of an internal structure of the X-ray CT scanner.

FIG. 2 shows a structure of the image acquisition processor 22 including a central processing unit (CPU) 100 for controlling the entire processor, memories 102 (a read-only memory and a random access memory) connected through a bus to the CPU, and a co-processor 104 for calculation. The co-processor 104 is used for the calculation for image analysis. The CPU 100 is further connected to a keyboard 106, a mouse 108, the display device 24, a hard disk drive (HDD) 110 having a hard disk for storing programs and files, a compact disk drive 112 for accessing a compact disk 112a and a communication device 114 for communication with the external. The CPU 100 is further connected to an external storage device 116 for storing a large amount of data. Programs stored in storage media such as the hard desk or the compact disk include an image data acquisition program and an image reconstruction program for computerized tomography, and further a correction program to be explained later. The image data acquisition program performs calculations for preprocessed X-ray transmission image to provide three-dimensional X-ray absorption coefficient data in a substance through which the X-rays transmit. The image reconstruction program reconstructs the image by performing projections of the data to a projection plane and the like. The image data acquisition and the image reconstruction are known in prior art, and detail explanation thereof is omitted here.

In the image acquisition processor 22, a storage medium for storing the programs is, for example, the hard disk, but it may be a flexible disk or a various type of optical disk to be used in a drive therefore such as a flexible disk drive or an optical disk drive.

Figure 3:
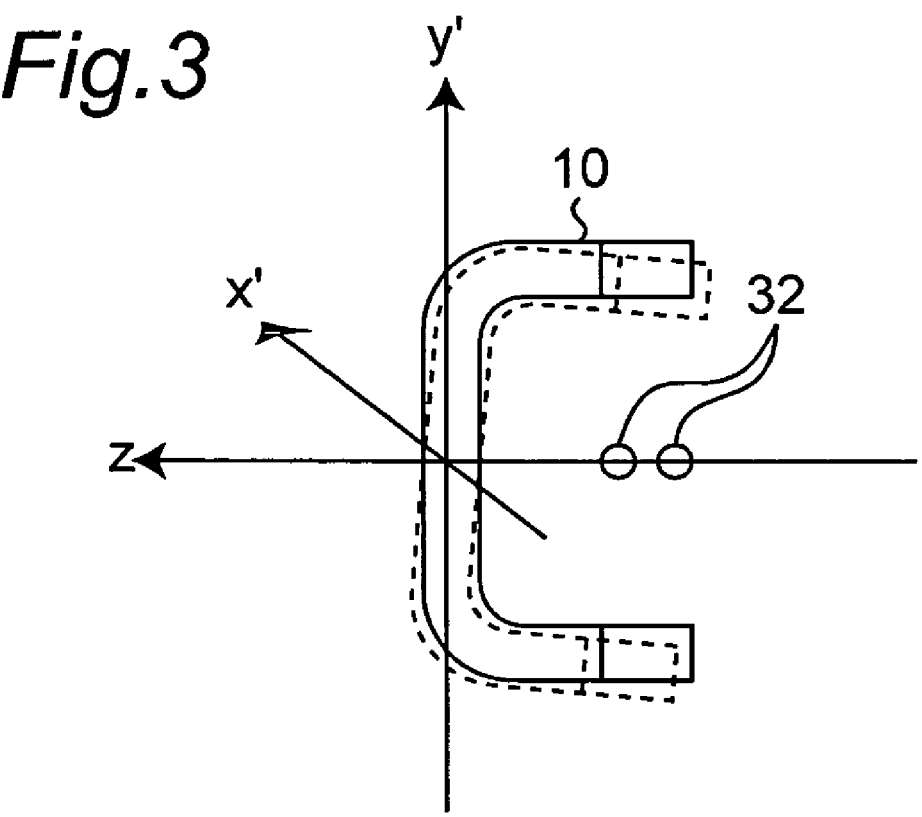
FIG. 3 is a diagram for explaining deviation of a C arm of the CT scanner.

In the above-mentioned CT scanner, when the rotary arm 10 is rotated around a horizontal rotary axis, experiments show that the rotary arm 10 makes bow-down movement, as shown schematically in FIG. 3 wherein x' and y' axes represent two directions perpendicular to z axis. The horizontal parts of the rotary arm 10 are displaced downward due to gravitational force. Because the X-ray source 12 and the two-dimensional X-ray detector 14 are mounted at the two ends of the rotary arm 10, their positions are shifted. Then the resultant image is fluctuated on the value in the direction of rotary axis (z value). If the rotary axis is vertical, no bow-down movement occurs. Thus, even if the rotary arm is bent and deformed, it is deformed by a constant amount in the vertical direction during the rotation, and there is no problem. On the contrary, in the horizontal CT mentioned above, it is necessary to correct the original image for the bow-down movement in the direction of rotary axis (z direction).

Before the correction for the image on the above-mentioned deviation in z axis, it is preferable that the displacements in the other two directions perpendicular to the rotary axis (z axis) are corrected by using the known process shown in Japanese Patent laid open Publication 2002-336237. In this correction, three correction tables are prepared by using two types of correction phantoms: a first table for correcting tube plane distortion of the two-dimensional X-ray detector and the magnetic distortion due to geomagnetism, a second table for correcting a shift of the rotary axis for X-ray CT imaging, and a third table for correcting the displacement of the rotary axis in axial direction. Then, the three tables are used for providing image correction tables for each of the rotation angles in X-ray CT imaging by rotating the coordinate axes with the second table for the first correction table and by moving the coordinate axes with the third table. By using the image correction tables, each of original X-ray images obtained by the two-dimensional X-ray detector is corrected, and the corrected X-ray images are provided for calculation to determine three-dimensional X-ray absorption coefficients in the object. The image correction tables can remove all distortion in x and y directions.

Figure 4:
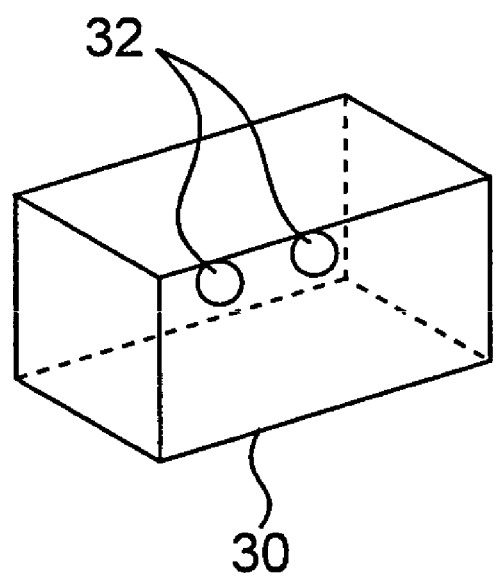
FIG. 4 is a perspective view of a correction phantom.

Next, correction of deviation in z direction is explained. The fluctuation due to the so-called "bow-down" is corrected by imaging a correction phantom 30 shown in FIG. 4, instead of the head rest 16, at the position of rotation center. The correction phantom 30 has a form of a regular prism, and it is made of an X-ray transmitting material or a material having a low X-ray absorption coefficient such as an acrylic resin. Two spherical balls 32 made of a material having a high X-ray absorption coefficient such as copper are embedded therein. The correction phantom 30 is positioned so that the two balls 32 are put around the rotary axis or generally on the rotary axis. Because the ball 32 which absorbs X-rays is spherical, the position thereof can be detected easily at a center of the image thereof by processing the image data. The correction phantom 30 is substantially the same as that shown in Japanese Patent laid open Publication 2002-336237, but the setting position is different. In concrete, the head rest 16 is detached from the X-ray CT scanner, and a phantom supporter (not shown) is provided instead of the head rest 16. Then phantom 30 is put on the supporter so that the two balls 32 are positioned together around the rotary axis. Next, the X-ray transmission image of the balls 32 is obtained while the rotation angle of the rotary arm 10 is changed.

Figure 5:
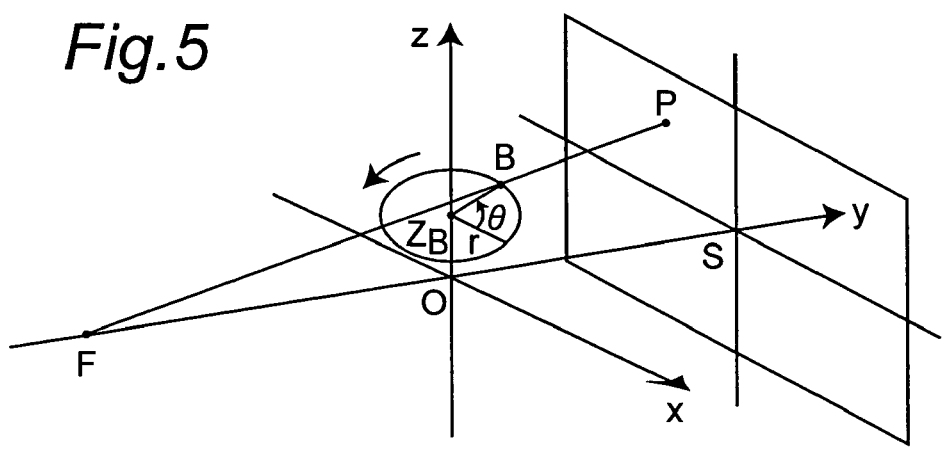
FIG. 5 is a diagram for explaining X-ray imaging of a correction phantom.

FIG. 5 shows a position relationship of the ball (B) 32 in the correction phantom 30 and a two-dimensional image in the imaging plane of the two-dimensional X-ray detector 14. Point F shows a position (focal point) at which a cone beam X-rays are generated by the X-ray source 12, and a rectangle represents the two-dimensional image. In FIG. 5, z axis (rotary axis) is a lateral direction for the two-dimensional image, x axis is vertical to the two dimensional image, and y axis is perpendicular to the x and z axes. The cone beam X-rays generated from the focal point F transmit the ball 32 (B) baying a high X-ray absorption coefficient to be incident on the imaging plane of the two-dimensional X-ray detector 14. The position of the ball is expressed with parameters $z_B$, r and θ, wherein $z_B$ is a position of the ball 32 in z coordinate, r is a distance of the ball from z axis, and θ is a rotation angle front x axis. Point O is a point at which X-rays from the focal point F pass through the rotary axis (z axis) perpendicularly thereto, and point S is a point at which the X-rays through the point O are incident on the imaging plane. Point P shows a locus of the ball in the imaging plane.

In the ideal state, the central position of the ball (B) relative to the rotation center O is expressed with Eq. (1) represented below.

$$B = \begin{pmatrix} x_B \\ y_B \\ z_B \end{pmatrix} = \begin{pmatrix} r \cdot \cos\theta \\ r \cdot \sin\theta \\ z_B \end{pmatrix}, \quad (1)$$

wherein r is a radius (distance) of a locus of the ball in a direction vertical to z axis (rotary axis), and θ is an angle of the ball around z axis. For example, r is obtained as a radius of a deviation in a direction vertical to z axis (rotary axis).

Figure 6:
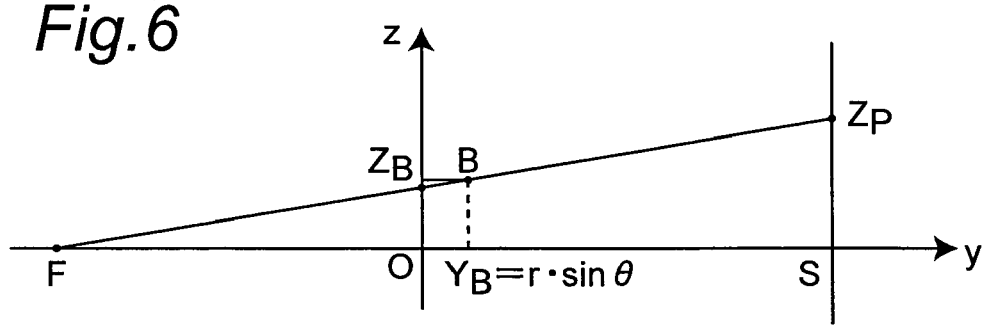
FIG. 6 is another diagram for explaining X-ray imaging of a correction phantom.

FIG. 6 shows a situation when the situation shown in FIG. 5 is observed in x+ direction, wherein $z_P$ is z coordinate of point P in the imaging plane. Therefore, Eq. (2) shown below holds for a distance FS between the focal point F and a point S in the imaging plane and a distance OF between the rotation center O and the focal point F:

$$z_P = \frac{\overline{FS}}{\overline{OF} + r \cdot \cos\theta} \cdot z_B. \quad (2)$$

A difference between $z_P$ (Eq. (2)) and the actual position of the ball (B) is used as a correction value in z direction.

Figure 7:
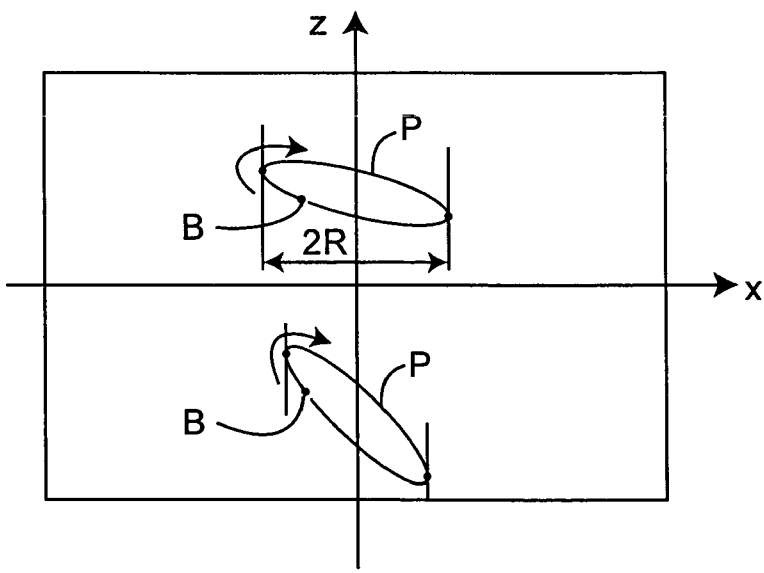
FIG. 7 is a diagram of loci of balls in the correction phantom.

When the image of the ball (B) 32 in the correction phantom 30 is observed in y+ direction, a locus P as shown in FIG. 7 is obtained. FIG. 7 shows the loci P of the two balls in at upper and lower positions along z axis.

Two limits of the deviation of the ball (B) in x direction are considered to be present in X-Z plane. The distance r (or radius r) of the ball B from z axis also meaning the width r of deviation of the ball B is obtained based on a width 2R of the deviation in the two-dimensional image which represents an extent of the movement in x direction of the locus P of the ball B shown in FIG. 7.

For example, because the distance r corresponds to the radius r of a circle shown in FIG. 5 in which the ball B is moved, the distance r is obtained based on a half of the maximum width 2R of the deviation in x direction of the locus of the ball B in the two-dimensional image shown in FIG. 7 when the rotary arm 10 makes one complete revolution around. For example, the distance r can be determined as shown in Eq. (3) by considering the magnifying power.

$r:2R*(½)=\overline{OF}:\overline{FS}.$ $r=2R*(½)*\overline{OF}/\overline{FS} \quad (3)$ In the above-mentioned example, when the rotary arm 10 makes one complete revolution around, the maximum of the width 2R of deviation is measured, and the distance r is determined based, on a half thereof. However, the rotary arm 10 may not necessarily be rotated by 360 degrees, and the rotary arm 10 may be rotated more than or less than 360 degrees. For example, when the rotary arm 10 is rotated precisely by 180 degrees from one of the two limits of deviation, the distance r is determined based on the locus, without measuring the width 2R of the deviation to halve the width 2R.

Further, the average position of the ball in z axis in the two-dimensional image may be determined generally as an average of z coordinate at the two limits in x direction (refer to FIG. 7). The average position corresponds to the above-mentioned $z_P$ at θ of 90 degrees. Alternatively, the average position may be obtained as an average of z coordinate of the entire trajectory. Then, the position $z_B$ of the ball in the rotary axis is determined based on the average position according to Eq. (2) at θ of 90 degrees.

Alternatively, R may be obtained by using the method of least squares. When R is determined, for example, from the locus P at the upper side in FIG. 7, Eq. (4) shown below is used as a measurement equation in x direction:

$$x = \sin\theta * a + \cos\theta * b + c \quad (4)$$

If the number of frames in 360 degrees is N, N equations hold for N rotation angles θ ($=\theta_0, \theta_1, \ldots, \theta_{N-1}$). As to the N equations, "a", "b" and "c" are determined by using the method of least squares. Then, R is obtained according to following Eq. (5):

$$R = (a^2 + b^2)^{1/2} \quad (5)$$

The initial angle θ of the ball can be calculated when the frame numbers of the images both at the left and right ends are found. The right point is set to zero degree, and the left point is set to 180 degrees. If N images are obtained per 360 degrees (or 2π), each frame is different by an angle of 2π/N. Thus, the angle at the zeroth frame is obtained as follows.

A) When right points are used, the angle at the zeroth frame = −(the number of right points) ∗ 2π/N,   (6)

and

B) when left points are used, the angle at the zeroth frame =   (7)

−(the number of left points) ∗ 2π/N + π.

It has to be considered that the values calculated with the relationships (6) and (7) may be different from each other by 2π. The angle at the m-th frame is expressed as follows:

The angle at the m-th frame =   (7)

(the angle of zeroth frame) + m ∗ 2π/N.

As explained above, the position of the ball is determined based on the two-dimensional imaging plane.

Next, a difference between $z_P$ and the imaged position of the actual ball B is obtained and it is set to a correction value in z direction. Then, a correction table is prepared on the rotation angle and the correction value for the deviation in z direction. When image data are acquired, the position is corrected by using the correction table.

Figure 8:
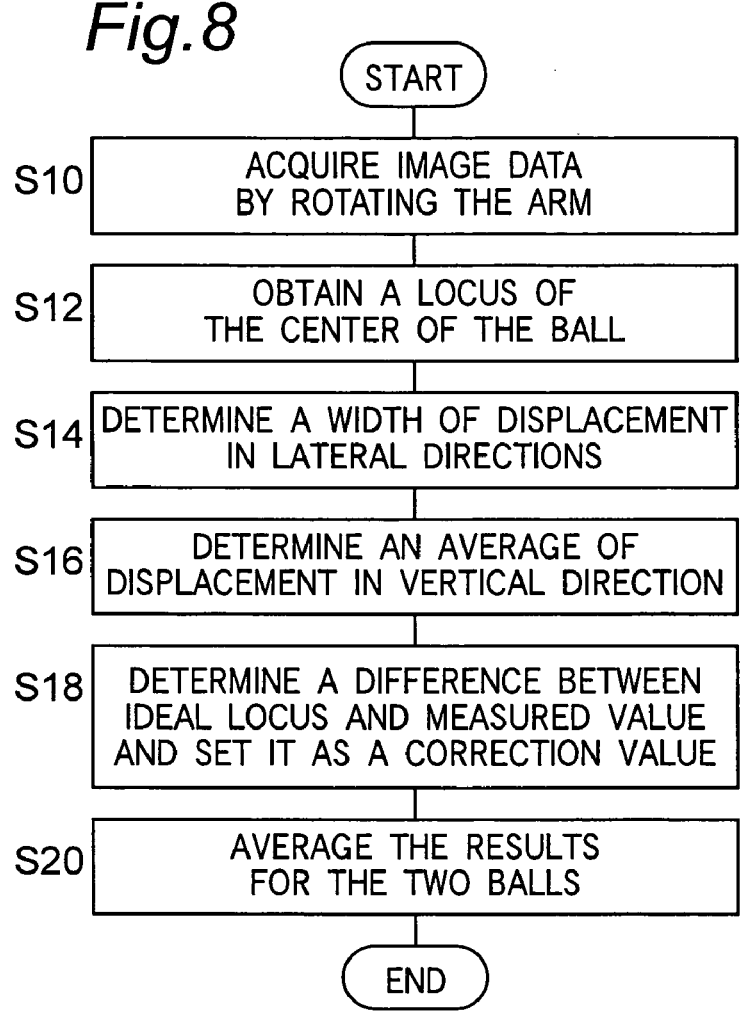
FIG. 8 is a flowchart of position correction in the direction of rotary axis.

FIG. 8 shows a flowchart on image correction executed by CPU 100. It is assumed here that the deviation in the two directions vertical to the rotary axis (z axis) has been corrected with a known correction method disclosed in Japanese Patent laid open Publication 2002-336237. First, the two balls in the correction phantom 30 are placed generally on the rotary axis, and the rotary arm 10 is rotated to acquire X-ray image data (step S10), and a locus P of the center of the two balls 32 is obtained (step S12).

Next, a width of deviation of the obtained locus P (radius $r_1$, $r_2$) for each of the balls 32 is obtained in lateral directions (directions vertical to z axis) in the two-dimensional image (step S14). (The subscripts "1" and "2" represent one and the other of the two balls.)

Next, an average $z_{b1}$, $z_{b2}$ of the deviation of the locus is obtained in the vertical direction (z direction) in the two-dimensional image (step S16).

Next, the ideal locus of the ball 32 is calculated by using Eq. (2) shown below, $$Z_P = \frac{\overline{FS} * Z_B}{\overline{OF} + r \cdot \sin\theta}, \quad (2)$$

wherein $z_p$ is z coordinate of the ideal locus of the ball 32, FS is distance from the focal point F to the imaging plane, $z_b$ is an average of the position of the ball 32 around the rotation of 360 degrees of the arm, OF is distance from the rotation center to the focal point, r is a radius of the deviation of the locus P measured on the ball 32 in a direction perpendicular to z axis, and θ is rotation angle of the rotary arm. A difference between the measured value z and the z coordinate $z_p$ of the locus of the ideal ball in Eq. (2) is obtained, and it is set to a correction value in the z direction (step S18). This equation is calculated on each of the two balls, and an average for the two balls is used as the correction value (step S20). Then, a correction table of the rotation angle and the correction value of the position deviation in z direction is created. When CT imaging data are acquired on an actual object, the position in z direction is corrected with the correction table.

Figure 9:
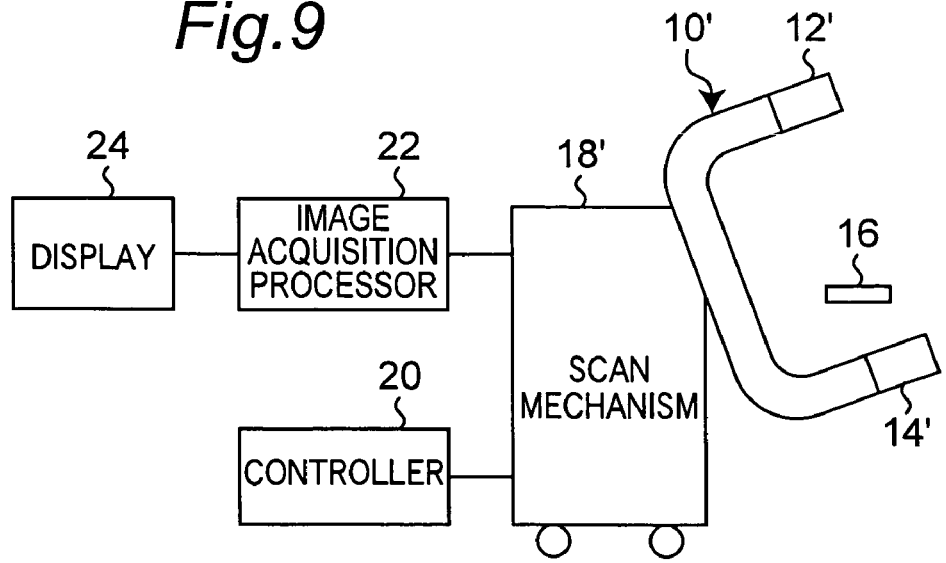
FIG. 9 is a block diagram of a modified embodiment of a portable X-ray CT scanner.

A CT scanner having a rotary arm with a horizontal rotary axis is explained above. Further, the deviation of position in the vertical direction can be corrected similarly for a CT scanner, as shown in FIG. 9, wherein a scan mechanism 18' supports a rotary arm 10' having an oblique or non-vertical rotary axis.

Figure 10:
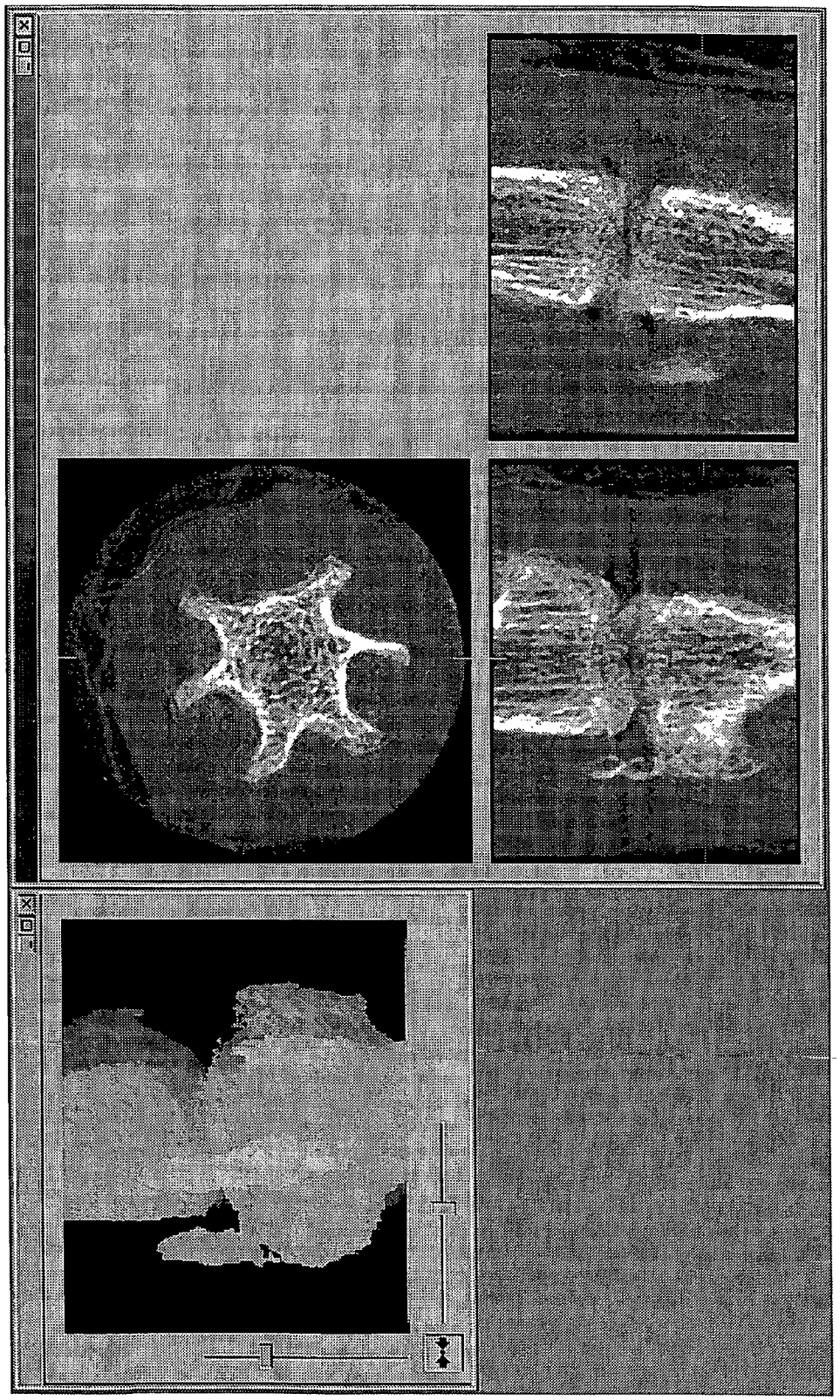
FIG. 10 is a diagram of a CT image without correcting the position in the rotary axis.
Figure 11:
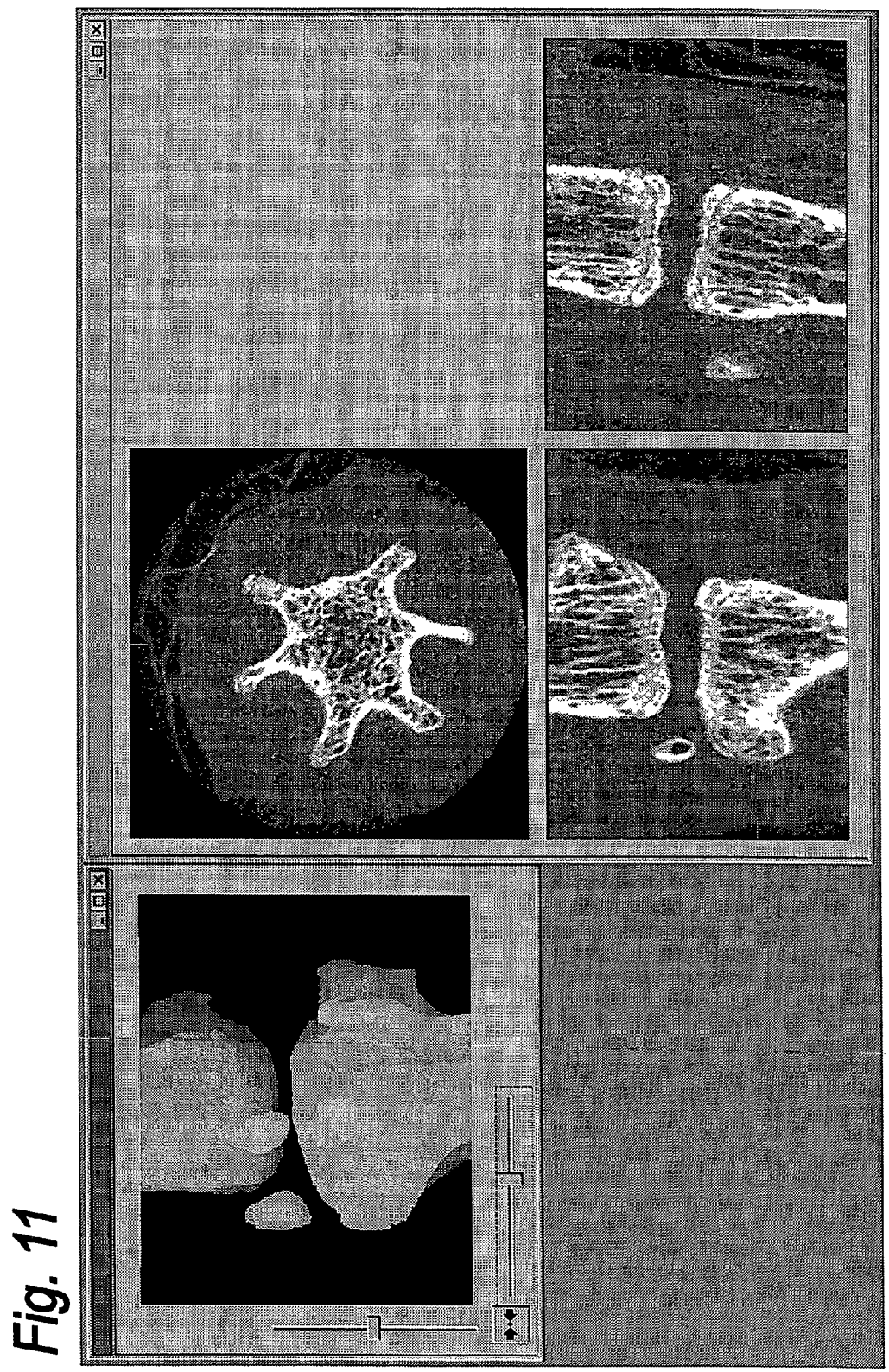
FIG. 11 is a diagram of a CT image after correcting the position in the rotary axis.

FIGS. 10 and 11 show examples of CT images for a comparative case without using the above-mentioned correction in the vertical direction and for a case according to the invention on the above-mentioned correction in the vertical direction, respectively. By comparing the images shown in FIG. 11 with the counterparts shown in FIG. 10, it is apparent that a remarkable improvement on image quality is observed in FIG. 11 when compared with comparative data shown in FIG. 10.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method for correcting an X-ray image in an X-ray computerized tomography scanner having a rotary arm and a scan mechanism, the rotary arm having an X-ray source generating cone beam X-rays and a two-dimensional X-ray detector opposing to the X-ray source, the scan mechanism supporting and rotating the rotary arm on a non-vertical rotary axis, wherein two-dimensional X-ray image data from the X-ray detector are acquired and processed while the scan mechanism rotates the rotary arm, the method comprising the steps of:

putting a correction phantom around the rotary axis or substantially on the rotary axis between the X-ray source and the two-dimensional X-ray detector, the correction phantom being made of an X-ray transmitting material and embedding an object which absorbs X-rays;

acquiring the image data of the object by generating X-rays by the X-ray source and receiving the X-rays transmitting the object by the X-ray detector while rotating the rotary arm, the image data extending in a direction of the rotary axis of the rotary arm and in another direction perpendicular to the rotary axis;

determining a locus of the object in the two-dimensional image;

estimating an ideal locus of the object in the direction of the rotary axis based on the determined locus in the two-dimensional image data;

determining a difference between the calculated position of the ideal locus and a counterpart position of the determined locus in the direction of the rotary axis; and reconstructing an X-ray CT image of the object based on the two dimensional image data of the object wherein a position of the X-ray CT image in the direction of the rotary axis is corrected based on the determined difference between the calculated position and the counterpart position in the direction of the rotary axis; wherein the step of determining the ideal locus comprises the steps of:

determining a width 2R of deviation in a direction perpendicularly to the rotary axis in the determined locus of the object in the two-dimensional image;

determining a distance r of the object from the rotary axis based on the width 2R of the deviation in the two-dimensional image;

determining an average position in the direction of the rotary axis of the determined locus in the two-dimensional image;

determining a position $z_B$ of the object in z axis based on the average position;

determining a rotation angle θ of the rotary arm based on the determined locus in the two-dimensional image; and calculating a position $z_P$ of the locus of the object in the direction of the rotary axis according to a following relationship:

$$Z_P = \frac{\overline{FS} * Z_B}{\overline{OF} + r \cdot \sin\theta},$$

wherein FS is distance from focal point F of the X-ray source to the imaging plane, OF is distance from the rotary axis to the focal point, and θ is rotation angle of the rotary arm, to determine the position $z_P$ as the ideal locus of the object in the direction of the rotary axis.

2. The method according to claim 1, further comprising the step of creating a table to correlate a rotation angle with the difference.

3. The method according to claim 1, wherein the rotary axis is horizontal.

4. A computer-readable storage medium for an X-ray computerized tomography scanner having a rotary arm and a scan mechanism, the rotary arm having an X-ray source generating cone beam X-rays and a two-dimensional X-ray detector opposing to the X-ray source, the scan mechanism supporting and rotating the rotary arm on a non-vertical rotary axis. wherein imaging data from the X-ray detector are acquired and processed while the scan mechanism rotates the rotary arm, storing a program comprising the steps of:

receiving image data of an object which absorbs X-rays, the image data extending in a direction of rotary axis of the rotary arm and in a direction perpendicular to the rotary axis;

determining a locus of the object in the two-dimensional image;

estimating an idea locus of the object in the direction of the rotary axis based on the determined locus in the two-dimensional image data;

determining a difference between the calculated position of the ideal locus and a counterpart position of the determined locus in the direction of the rotary axis and reconstructing an X-ray CT image of the object based on the two dimensional image data of the object wherein a position of the X-ray CT image in the direction of the rotary axis is corrected based on the determined difference between the calculated position and the counterpart position in the direction of the rotary axis; and wherein the step of estimating an ideal locus comprises the steps of:

determining a width 2R of deviation in a direction perpendicularly to the rotary axis in the determined locus of the object in the two-dimensional image;

determining a distance r of the object from the rotary axis based on the width 2R of the deviation in the two-dimensional image;

determining an average position in the direction of the rotary axis of the determined locus in the two-dimensional image;

determining a position $z_B$ of the object in z axis based on the average position;

determining a rotation angle θ of the rotary arm based on the determined locus in the two-dimensional image; and calculating a position $z_p$ of the locus of the object in the direction of the rotary axis according to a following relationship:

$$Z_P = \frac{\overline{FS} * Z_B}{\overline{OF} + r \cdot \sin\theta},$$

wherein FS is distance from focal point F of the X-ray source to the imaging plane, OF is distance from the rotary axis to the focal point, and θ is rotation angle of the rotary arm, to determine the position $z_p$ as the ideal locus of the object in the direction of the rotary axis.

5. The computer-readable storage medium according to claim 4, the program further comprising the step of creating a table to correlate a rotation angle with the difference.

6. An X-ray computerized tomography scanner comprising:

a rotary arm having an X-ray source generating cone beam X-rays and a two-dimensional X-ray detector opposing to the X-ray source;

a scan mechanism supporting and rotating the rotary arm, the rotary arm having a non-vertical rotary axis;

a storage device for storing a correction table on rotation angle and position deviation only in the direction of the rotary axis;

an acquisition device which acquires image data from the X-ray detector while the rotary arm is rotated by the scanning mechanism and corrects the position in the direction of the rotary axis to shift the image data by the position deviation only in the direction of the rotary axis irrespective of distortion of the image data by using the correction table stored in said storage device; and a display device which displays an image reconstructed from the image data acquired by said data acquisition device.

7. The scanner according to claim 6, wherein the rotary axis is horizontal.

8. An X-ray computerized tomography scanner comprising:
   a rotary arm having an X-ray source generating cone beam X-rays and a two-dimensional X-ray detector opposing to the X-ray source;
   a scan mechanism supporting and rotating the rotary arm, the rotary arm having a non-vertical rotary axis;
   an acquisition device which acquires image data from the X-ray detector while the rotary arm is rotated by the scan mechanism, the image data extending in a direction of the rotary axis of the rotary arm and in another direction perpendicular to the rotary axis;
   a data processor which processes the image data acquired by said acquisition device on a correction phantom put substantially on the rotary axis, the correction phantom being made of an X-ray transmitting material and embedding an object which absorbs X-rays, wherein the data processor determines a locus of the object in the two-dimensional image, estimates an ideal locus of the object in the direction of the rotary axis based on the determined locus in the two-dimensional image data, and determines a difference between the calculated position of the ideal locus and a counterpart position of the determined locus in the direction of the rotary axis;
   a storage device for storing a correction table on rotation angle and position deviation only in the direction of the rotary axis based on the difference determined by said data processor; and
   an image reconstructor which reconstructs an X-ray CT image of an object based on the image data acquired by said acquisition device on the object wherein the image data is corrected in the direction of the rotary axis with the correction table stored in said storage device.

* * * * *